(12) United States Patent
Alexander et al.

(10) Patent No.: US 9,220,890 B2
(45) Date of Patent: Dec. 29, 2015

(54) EXTENSIBLE IMPLANTABLE MEDICAL LEAD WITH CO-AXIAL CONDUCTOR COILS

(75) Inventors: James A. Alexander, Shorewood, MN (US); Michael E. Metzler, Minneapolis, MN (US); Jon P. Dorff, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 282 days.

(21) Appl. No.: 12/937,158

(22) PCT Filed: Jan. 23, 2009

(86) PCT No.: PCT/US2009/031783
§ 371 (c)(1),
(2), (4) Date: Nov. 18, 2010

(87) PCT Pub. No.: WO2009/128967
PCT Pub. Date: Oct. 22, 2009

(65) Prior Publication Data
US 2011/0066195 A1 Mar. 17, 2011

Related U.S. Application Data

(60) Provisional application No. 61/045,644, filed on Apr. 17, 2008.

(51) Int. Cl.
*A61N 1/00* (2006.01)
*A61B 5/04* (2006.01)
(Continued)

(52) U.S. Cl.
CPC ............ *A61N 1/0534* (2013.01); *A61N 1/0551* (2013.01); *A61N 1/0472* (2013.01); *A61N 1/0488* (2013.01)

(58) Field of Classification Search
CPC . A61N 1/0534; A61N 1/0551; A61N 1/0472; A61N 1/0488
USPC ............................ 600/373, 377; 607/115, 116
See application file for complete search history.

(56) References Cited

U.S. PATENT DOCUMENTS 4,640,983 A * 2/1987 Comte ....................... 174/119 R
4,945,342 A * 7/1990 Steinemann ............... 174/113 R
(Continued)

FOREIGN PATENT DOCUMENTS

WO WO02/28638 4/2002

*Primary Examiner* — Niketa Patel
*Assistant Examiner* — Lindsey G Hankins
(74) *Attorney, Agent, or Firm* — Mueting, Raasch & Gebhardt, P.A.

(57) ABSTRACT

An extensible implantable electrical lead includes a lead body having a proximal end and a distal end. The lead body is formed of a polymeric material that is extensible between a first length and a second length. A plurality of electrical conductors are disposed within the lead body and extend between the proximal end and the distal end. The plurality of electrical conductors are each electrically insulated from each other and form co-axial coils between the proximal end and the distal end. The co-axial coils include an outer coil disposed about an inner coil. The inner coil has a first plurality of electrical conductors that are electrically insulated and separated from each other and have a first coil diameter. The outer coil includes a second plurality of electrical conductors that are electrically insulated and separated from each other and have a second coil diameter. The second coil diameter is greater than the first coil diameter, and the first plurality is a number less than the second plurality.

18 Claims, 5 Drawing Sheets

(51) Int. Cl.
*A61N 1/05* (2006.01)
*A61N 1/04* (2006.01)

(56) References Cited

U.S. PATENT DOCUMENTS

| | | |
|---|---|---|
| 6,249,708 B1 | 6/2001 | Nelson et al. |
| 6,813,521 B2 | 11/2004 | Bischoff et al. |
| 7,184,838 B2 | 2/2007 | Cross |
| 7,292,894 B2 | 11/2007 | Belden |
| 7,519,432 B2 | 4/2009 | Bolea et al. |
| 7,546,163 B2 | 6/2009 | Bischoff et al. |
| 2004/0147992 A1 | 7/2004 | Bluger et al. |
| 2005/0222647 A1 | 10/2005 | Wahlstrand et al. |
| 2005/0222656 A1 | 10/2005 | Wahlstrand et al. |
| 2006/0200218 A1* | 9/2006 | Wahlstrand ............ 607/116 |
| 2006/0247748 A1 | 11/2006 | Wahlstrand et al. |
| 2008/0039917 A1* | 2/2008 | Cross et al. ............ 607/122 |

* cited by examiner

EXTENSIBLE IMPLANTABLE MEDICAL LEAD WITH CO-AXIAL CONDUCTOR COILS

This application claims the benefit of and is a U.S. National Stage filing under 35 U.S.C. 371 of copending PCT Application Serial No. PCT/US2009/031783, filed Jan. 23, 2009, which in turn claims the benefit of U.S. Provisional Application No. 61/045,644, filed Apr. 17, 2008, "Extensible Implantable Medical Lead with Co-Axial Conductor Coils," the disclosure of all of the above which is incorporated by reference herein in its entirety.

FIELD

The present disclosure relates to extensible implantable medical leads with co-axial conductor leads.

BACKGROUND

Implantable medical devices are commonly used today to treat patients suffering from various ailments. Such implantable devices may be utilized to treat conditions such as pain, incontinence, sleep disorders, and movement disorders such as Parkinson's disease and epilepsy, for example. Such therapies also appear promising in the treatment of a variety of psychological, emotional, and other physiological conditions.

One known type of implantable medical device, a neurostimulator, delivers mild electrical impulses to neural tissue using an electrical lead. For example, to treat pain, electrical impulses may be directed to specific sites. Such neurostimulation may result in effective pain relief and a reduction in the use of pain medications and/or repeat surgeries.

Typically, such devices are totally implantable and may be controlled by a physician or a patient through the use of an external programmer Current systems generally include a primary cell neurostimulator, a lead extension, and a stimulation lead, and two particular applications of systems may be referred to as: (1) spinal cord stimulation; and (2) deep brain stimulation.

A spinal cord stimulator may be implanted in the abdomen, upper buttock, or pectoral region of a patient and may include at least one extension running from the neurostimulator to the lead or leads which are placed somewhere along the spinal cord. Each of the leads (to be discussed in detail hereinafter) often includes from one to sixteen, or more electrodes. Each extension (likewise to be discussed in detail hereinafter) is plugged into or connected to the neurostimulator at a proximal end thereof and is coupled to and interfaces with the lead or leads at a distal end of the extension or extensions.

The implanted neurostimulation system is configured to send mild electrical pulses to the spinal cord. These electrical pulses are delivered through the lead or leads to regions near the spinal cord or the nerve selected for stimulation. Each lead includes a small insulated wire coupled to an electrode at the distal end thereof through which the electrical stimulation is delivered. The lead may also include a corresponding number of internal wires to provide separate electrical connection to each electrode such that each electrode may be selectively used to provide stimulation. Connection of the lead to an extension may be accomplished by means of a connector block including, for example, a series or combination of set-screws, ball-seals, etc. The leads are inserted into metal set screw blocks, and metal set screws are manipulated to press the contacts against the blocks to clamp them in place and provide an electrical connection between the lead wires and the blocks.

A deep brain stimulation system includes similar components (i.e. a neurostimulator, at least one extension, and at least one stimulation lead) and may be utilized to provide a variety of different types of electrical stimulation to reduce the occurrence or effects of Parkinson's disease, epileptic seizures, or other undesirable neurological events. In this case, the neurostimulator may be implanted into the pectoral region of the patient. The extension or extensions may extend up through the patient's neck, and the leads/electrodes are implanted in the brain. The leads may interface with the extension just above the ear on both sides of the patient. The distal end of the lead may contain from four to sixteen, or more electrodes and, as was the case previously, the proximal end of the lead may connect to the distal end of the extension and held in place by set screws. The proximal portion of the extension plugs into the connector block of the neurostimulator.

Both of the spinal cord stimulation and deep brain stimulation implanted systems traverse portions of the human body that stretch and relax. To account for this stretching and relaxing, the lead and lead extension can be looped to allow for stretching and relaxing with the human body.

BRIEF SUMMARY

The present disclosure relates to extensible implantable medical leads with co-axial conductor leads.

In an exemplary embodiment, an extensible implantable electrical lead includes a lead body having a proximal end and a distal end. The lead body is formed of a polymeric material that is extensible between a first length and a second length. A plurality of electrical conductors are disposed within the lead body and extend between the proximal end and the distal end. The plurality of electrical conductors are each electrically insulated from each other and form co-axial coils between the proximal end and the distal end. The co-axial coils include an outer coil disposed about an inner coil. The inner coil has a first plurality of electrical conductors that are electrically insulated and separated from each other and have a first coil diameter. The outer coil includes a second plurality of electrical conductors that are electrically insulated and separated from each other and have a second coil diameter. The second coil diameter is greater than the first coil diameter, and the first plurality is a number less than the second plurality.

In another exemplary embodiment, an extensible implantable electrical lead includes a lead body having a proximal end and a distal end. The lead body is formed of a polymeric material that is extensible between a first length and a second length. A plurality of electrical conductors are disposed within the lead body and extend between the proximal end and the distal end. The plurality of electrical conductors are each electrically insulated from each other and form co-axial coils between the proximal end and the distal end. The co-axial coils include an outer coil disposed about an inner coil. The inner coil has a first plurality of electrical conductors that are parallel wound in a first direction and are electrically insulated and separated from each other and have a first coil diameter. The outer coil includes a second plurality of electrical conductors that are parallel wound in a second direction, opposing the first direction, and are electrically insulated and separated from each other and have a second coil diameter. The second coil diameter is greater than the first coil diameter, and the first plurality is a number less than the second plurality.

In another exemplary embodiment, an implantable neurostimulation system includes a neurostimulating device and an extensible electrical lead, described herein, electrically coupled to the neurostimulating device.

In another exemplary embodiment, a method includes applying a force of 5 N or less to a proximal end and a distal end of an extensible electrical lead having a first length. The force increases the first length of the extensible electrical lead by at least 10%. Then the force is removed from the extensible electrical lead to return the extensible electrical lead to its first length.

BRIEF DESCRIPTION OF THE DRAWING

The disclosure may be more completely understood in consideration of the following detailed description of various embodiments of the invention in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying drawings that form a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The term "lead" refers to either or both a lead and a lead extension as described below, unless otherwise noted.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The term "active implantable medical device" or "implantable signal generator" are used interchangeably and includes, for example, a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, and the like.

The present disclosure relates to extensible implantable medical leads with co-axial conductor leads where the lead or lead extension is extensible between a stretched state and a relaxed state. These extensible leads are particularly useful as implantable leads for neurostimulator applications where the leads provide spinal cord stimulation and deep brain stimulation and traverse portions of the human body that stretch and relax, though said leads are not limited to such applications. To account for this stretching and relaxing within the patient, the lead is repeatedly extensible. The extensible leads described herein are formed by at least an outer coil disposed co-axially about an inner coil. The outer and inner coils are each formed of a plurality of insulated conductors and the outer coil has more conductors than the inner coil. This arrangement allows the shear stress of the inner coil to be matched with the shear stress of the outer coil to improve performance of the extensible lead. The co-axial coil is disposed within a stretchable or extensible outer sheath that has an extensibility of at least 10% or at least 20% or at least 25%, or more (with an applied force of 5 N or less). Thus, the extensible lead can be stretched by at least 10% or at least 20% or at least 25%, or more and return to its original length when relaxed. While the present disclosure is not so limited, an appreciation of various aspects of the disclosure will be gained through a discussion of the examples provided below.

Figure 1:
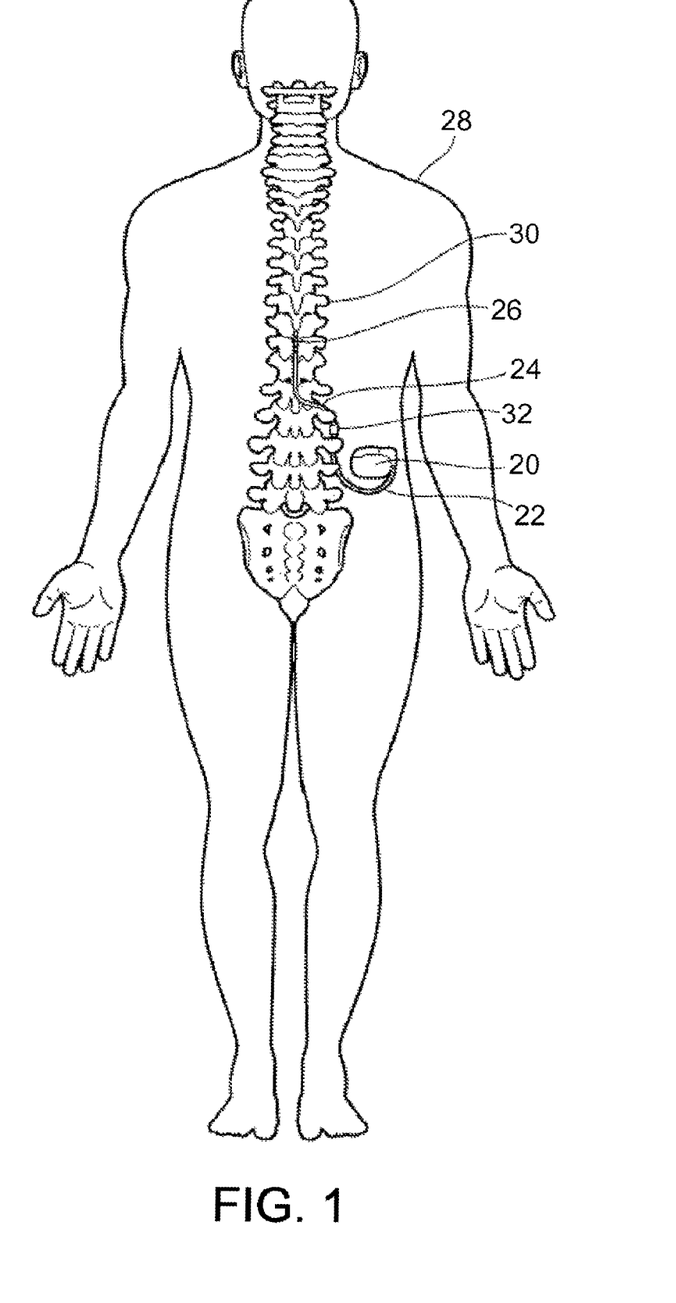
FIG. 1 is a schematic diagram of a spinal cord stimulation system implanted within a human body.

FIG. 1 is a schematic diagram of a spinal cord stimulation system implanted within a human body or patient 28. The implanted spinal cord stimulation system includes an active medical device 20 such as a neurostimulator. The active medical device 20 is coupled to a lead extension 22 having a proximal end coupled to the active medical device 20, and a lead 24 having a proximal end coupled to a distal end or lead connector 32 of the lead extension 22 and a distal end of the lead 24 coupled to one or more electrodes 26.

In some embodiments, the lead 24 proximal end is coupled to the active medical device 20, without a need for the lead extension 22. The spinal cord neurostimulator 20 is illustrated being implanted within the torso or abdomen of the patient or human body 28. The lead 24 is shown placed somewhere along the spinal cord 30. In many embodiments, the active medical device 20 has one or two leads 24 each having four to sixteen, or more, electrodes.

Such a system may also include a physician programmer and a patient programmer (not shown). The active medical device 20 can be considered to be an implantable signal generator of the type available from Medtronic, Inc., and capable of generating multiple signals occurring either simultaneously or one signal shifting in time with respect to the other, and having independently varying amplitudes and signal widths. The active medical device 20 contains a power source and the electronics for sending precise, electrical signals to the patient to provide the desired treatment therapy. While the active medical device 20, in many embodiments, provides electrical stimulation by way of signals, other forms of stimulation may be used as continuous electrical stimulation.

Figure 2:
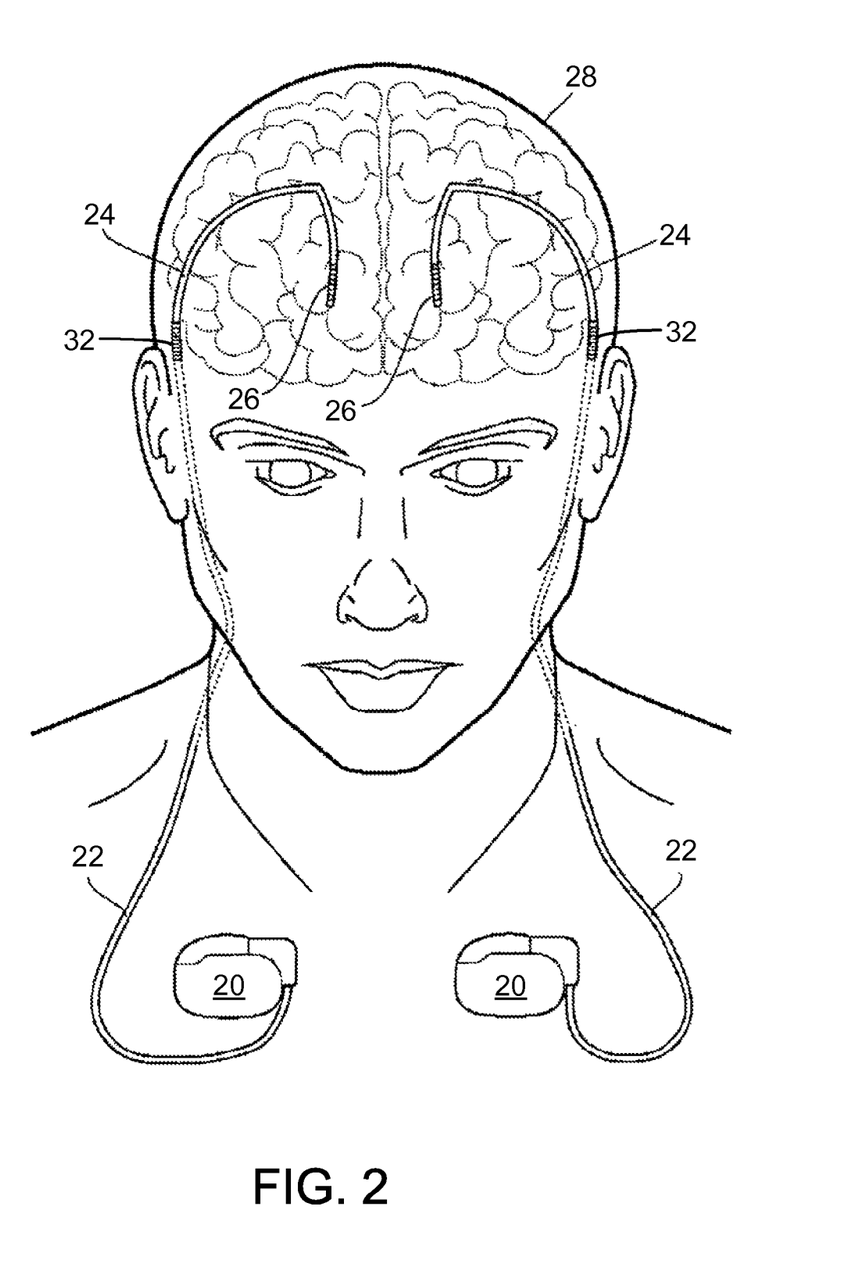
FIG. 2 is a schematic diagram of a deep brain stimulation system implanted within a human body.

FIG. 2 is a schematic diagram of a deep brain stimulation system implanted within a patient or human body 28. The implanted deep brain stimulation system includes an active medical device 20 such as a neurostimulator. The active medical device 20 is coupled to a lead extension 22 having a proximal end coupled to the active medical device 20, and a lead 24 having a proximal end coupled to a distal end or lead connector 32 of the lead extension 22 and a distal end of the lead 24 coupled to one or more electrodes 26.

In some embodiments, the lead 24 proximal end is coupled to the active medical device 20, without a need for the lead extension 22. The deep brain neurostimulator 20 is illustrated being implanted within the pectoral region of the patient or human body 28. The lead 24 is shown placed somewhere on or within the brain. In many embodiments, the active medical device 20 has one or two leads 24 each having four to sixteen, or more, electrodes.

Such a system may also include a physician programmer and a patient programmer (not shown). The active medical device 20 can be considered to be an implantable signal generator of the type available from Medtronic, Inc. and capable of generating multiple signals occurring either simultaneously or one signal shifting in time with respect to the other, and having independently varying amplitudes and signal widths. The active medical device 20 contains a power source and the electronics for sending precise, electrical signals to the patient to provide the desired treatment therapy. While the active medical device 20, in many embodiments, provides electrical stimulation by way of signals, other forms of stimulation may be used as continuous electrical stimulation.

Figure 3:
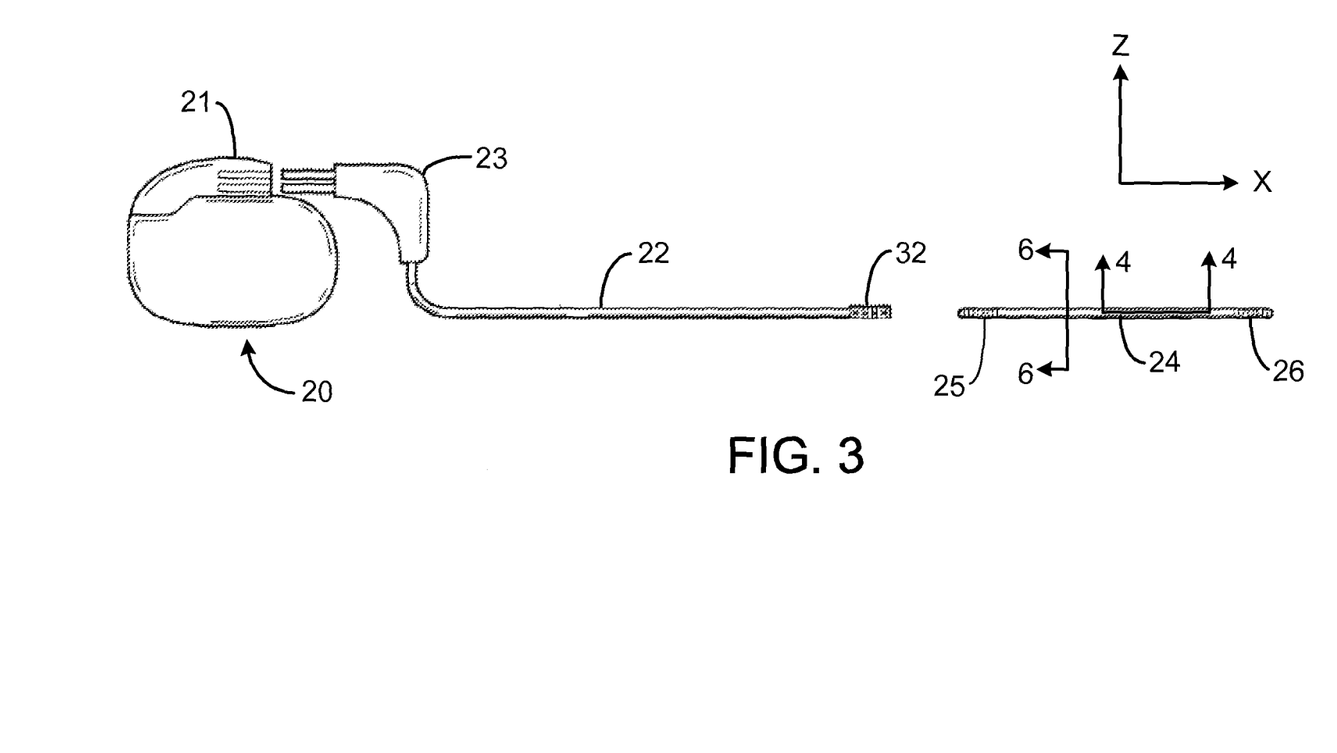
FIG. 3 is a schematic exploded view of an implantable active medical device.

FIG. 3 is a schematic exploded view of the implantable stimulation system described above that includes an exemplary lead extension 22 configured to be physically and electrically coupled between a neurostimulator 20 and lead 24. The implantable stimulation system described herein allows individual contacts 26 at the distal end of the lead 24 to be addressed individually by the neurostimulator 20 via the individual insulated electrical conductors extending through the lead 24 as described below.

A proximal portion of the lead extension 22 includes a connector 23 configured to be received or plugged into connector block 21 of neurostimulator 20. A distal end of the lead extension 22 includes a lead connector 32 including internal contacts configured to receive a proximal end of the lead 24 having contacts 25 thereon.

The lead 24 includes a plurality of insulated electrical conductors each coupled at their proximal end to a lead connector 32 via contacts 25 at its proximal end and to contacts/electrodes 26 at its distal end. Some leads are designed to be inserted into a patient percutaneously and some are designed to be surgically implanted. In some embodiments, the lead 24 may include a paddle (not shown) at its distant end for housing electrodes 26. In some embodiments, electrodes 26 may include one or more ring contacts at the distal end of lead 24. Each contact is electrically coupled to a single insulated electrical conductor extending through the lead 24 as described below.

Figure 5:
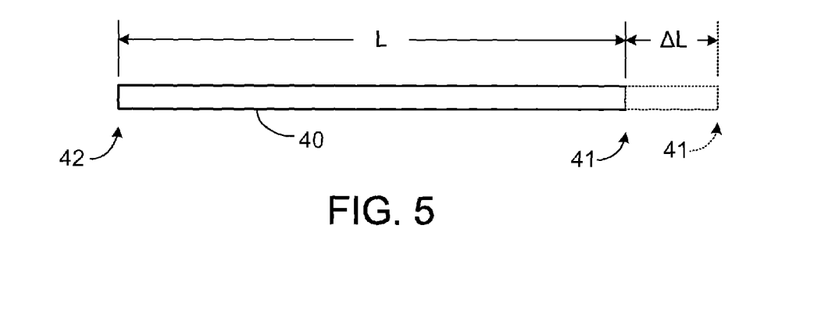
FIG. 5 is a schematic diagram of the extensible lead in a stretched state and a relaxed state.

The lead 24 and/or lead extension 22 has a body formed of an extensible polymeric material that allows the lead 24 and/or lead extension 22 to repeatedly stretch at least 10%, or least 20%, or at least 25%, or at least 50%, as illustrated in FIG. 5 and return to its original or relaxed length L. In some exemplary embodiments, the extensible polymeric material is silicone and the insulated electrical conductor are configured to allow the lead 24 and/or lead extension 22 to stretch and relax at least 10%, or least 20%, or at least 25%, or at least 50%, as illustrated in FIG. 5. The extensibility values reported herein are based on an applied force of 5 N or less.

Figure 4:
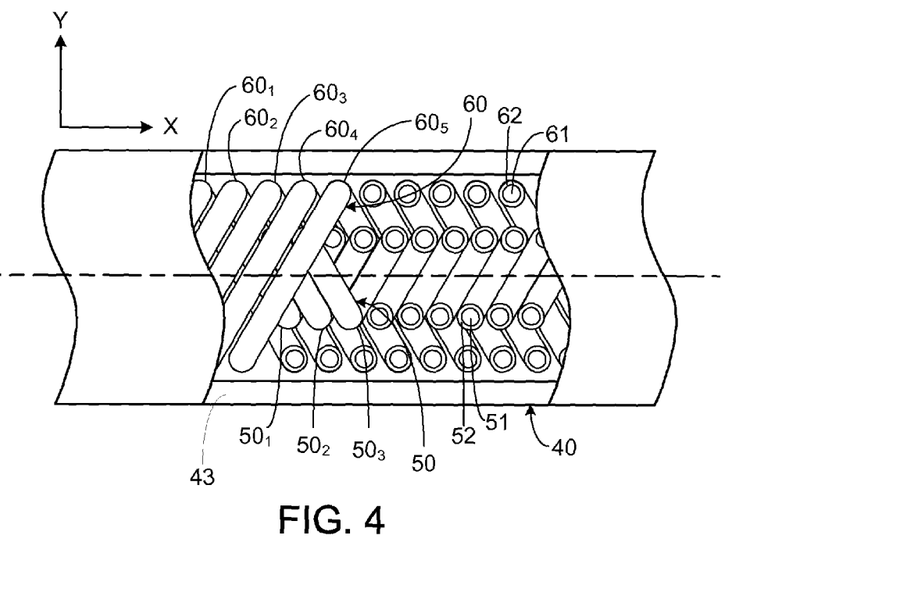
FIG. 4 is a schematic partial cross-sectional diagram of an exemplary extensible lead taken along line 4-4 of FIG. 3.
Figure 6:
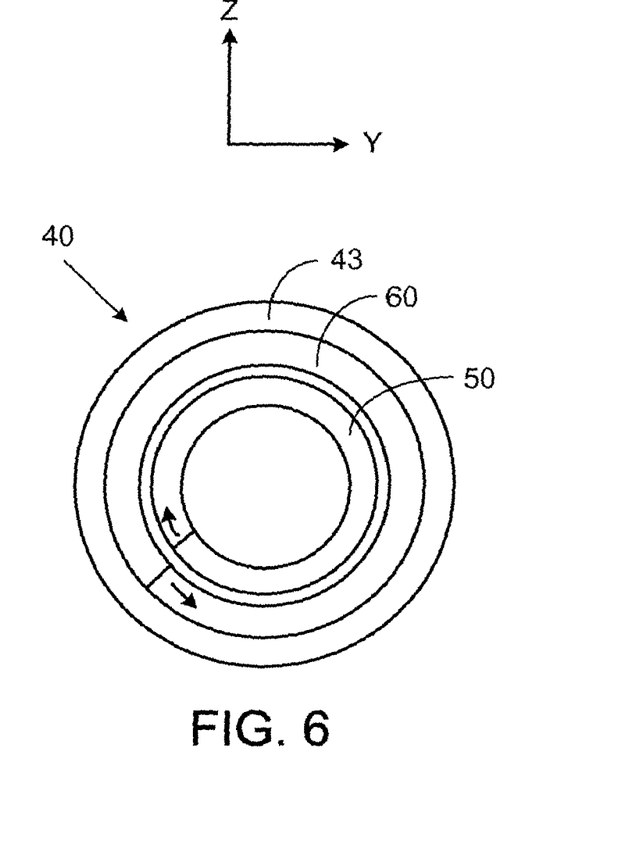
FIG. 6 is a schematic cross-sectional diagram of an examplary extensible lead taken along line 6-6 of FIG. 3.

FIG. 4 is a schematic partial cross-sectional diagram of the extensible lead taken along line 4-4 of FIG. 3. FIG. 5 is a schematic diagram of the extensible lead in a stretched state and a relaxed state. The extensible lead includes a lead body 40 extending between a proximal end 42 and a distal end 41. FIG. 6 is a schematic cross-sectional diagram of the extensible lead taken along line 6-6 of FIG. 3.

The lead body 40 is formed of a polymeric material that is repeatedly extensible between a first length L and a second length L+ΔL, where the second length is greater than the first length by at least 10%, or least 20%, or at least 25%, or at least 50%. This increase in length is accomplished by application of a force of 5 N or less. Upon removal of the force, the lead body 40 relaxes, contracts, or returns to its original length L. The lead body 40 can be cycled between the first length and the second length thousands of times or more.

The lead body 40 can include a sheath 43 surrounding the coaxial coils 50, 60. In some exemplary embodiments, both the sheath 43 and the coaxial coils 50, 60 are fixed at the proximal end 42 and a distal end 41 of the lead body 40. In many embodiments the sheath 43 is loosely disposed about the coaxial coils 50, 60 between the proximal end 42 and a distal end 41 of the lead body 40.

In some exemplary embodiments, the extensibility of the sheath 43 substantially matches the stretchability of the coaxial coils 50, 60. The sheath 43 is formed of an extensible polymeric material that allows the lead body 40 to stretch and relax at least 10%, or least 20%, or at least 25%, or at least 50%, as illustrated in FIG. 5. In many embodiments, the extensible polymeric material is silicone and the insulated electrical conductor are configured to allow the lead body 40 to stretch and relax at least 10%, or least 20%, or at least 25%, or at least 50%, as illustrated in FIG. 5.

A plurality of electrical conductors $60_1$, $60_2$, $60_3$, $60_4$, $60_5$, $50_1$, $50_2$, $50_3$ are disposed within the lead body 40 and extend between the proximal end and the distal end of the lead body 40. The plurality of electrical conductors $60_1$, $60_2$, $60_3$, $60_4$, $60_5$, $50_1$, $50_2$, $50_3$ are each electrically insulated from each other and form co-axial coils 60, 50 from the proximal end to the distal end.

The co-axial coils include an outer coil 60 disposed about an inner coil 50. The outer coil 60 can have any useful diameter such as, for example, from 1800 to 2500 micrometers. The inner coil 50 can have any useful diameter such as, for example, from 250 to 500 micrometers. In many embodiments, the outer coil 60 is wound in a clockwise or counter clockwise direction and the inner coil 50 is wound in direction opposing the outer coil 60 winding. In some embodiments a sheath (not shown) is disposed between the outer coil 60 and the inner coil 50. The sheath can be formed of an extensible polymeric material that is the same or similar to the extensible polymeric material forming the lead body 40.

The inner coil 50 includes a first plurality of electrical conductors $50_1$, $50_2$, $50_3$ that are electrically insulated and separated from each other. The outer coil 60 includes a second plurality of electrical conductors $60_1$, $60_2$, $60_3$, $60_4$, $60_5$ that are electrically insulated and separated from each other. The second coil diameter is greater than the first coil diameter, and the first plurality being a number less than the second plurality. The illustrated embodiment includes five outer second plurality of electrical conductors $60_1$, $60_2$, $60_3$, $60_4$, $60_5$ that are parallel wound in co-axial relation to the parallel wound three inner first plurality of conductors $50_1$, $50_2$, $50_3$. The number of inner coil 50 parallel wound conductors is chosen so that the inner coil 50 has a shear stress value that is substantially equal to the outer coil 60 shear stress.

While the illustrated exemplary embodiment includes an outer coil 60 having five parallel wound insulated electrical conductors, the outer coil can include any useful number (being greater than the number of inner coil 50 parallel wound insulated electrical conductors) of parallel wound insulated electrical conductors such as, for example, from 3 to 16, or from 4 to 12, or from 4 to 8, as desired. Likewise, while the inner coil 50 has three parallel wound insulated electrical conductors, the inner coil can include any useful number (being less than the number of outer coil parallel wound insulated electrical conductors) of parallel wound insulated electrical conductors such as, for example, from 1 to 8, or from 2 to 5, or from 2 to 4, as desired.

In some exemplary embodiments a third coil (not shown) can be disposed in co-axial relation to the inner and outer coils 50, 60 and be within the inner coil 50 or surrounding the outer coil 60. This third coil can have any number of insulated conductors that is less than the number of insulated conductors forming the inner coil 50 if it is placed within the inner coil 50 or greater than the number of insulated conductors forming the outer coil 60 if it is placed around the outer coil 60. In some embodiments the third coil can be formed of a single insulated conductor disposed within the inner coil 50 and in co-axial relation to the inner coil 50 and the outer coil 60.

The individual insulated conductors, described above, can have any useful diameter. In examplary embodiments, the electrical conductor 51, 61 has a diameter in a range from 50 to 250 micrometers, or from 100 to 150 micrometers and the insulator layer 52, 62 can add from 15 to 50 micrometers to the electrical conductor 51, 61 diameter. Thus, in many embodiments, the insulated electrical conductors $60_1$, $60_2$, $60_3$, $60_4$, $60_5$, $50_1$, $50_2$, $50_3$ have a diameter in a range from 65 to 300 micrometers, or from 115 to 200 micrometers. The insulator layer 52, 62 can be formed of any useful electrically insulating material such as, for example, a polymeric material. In some embodiments, the electrically insulating material includes silicone. In many embodiments, the electrical conductors 51, 61 and/or the insulated electrical conductors $60_1$, $60_2$, $60_3$, $60_4$, $60_5$, $50_1$, $50_2$, $50_3$, have the same or substantially the same diameter.

The lead body 40 extending between a proximal end 42 and a distal end 41. As shown in FIG. 3 and FIG. 5, stimulating electrodes 26 are located at the distal end 41 and contacts 25 are located at the proximal end 42. Each insulated electrical conductors $60_1$, $60_2$, $60_3$, $60_4$, $60_5$, $50_1$, $50_2$, $50_3$ used to form the co-axial coils 60, 50 can be addressed between a single contact 25 and a single electrode 26 such that each electrode 26 can be individually activated via the contact and a single insulated electrical conductor.

Thus, exemplary embodiments of the EXTENSIBLE IMPLANTABLE MEDICAL LEAD WITH CO-AXIAL CONDUCTOR COILS are disclosed. One skilled in the art will appreciate that the present disclosure can be practiced with other embodiments. The disclosed embodiments are presented for purposes of illustration and not limitation, and the present disclosure is limited only by the claims that follow.

What is claimed is:

1. An extensible implantable electrical lead comprising:
   a lead body having a proximal end and a distal end, the lead body formed of a polymeric material that is extensible between a first length and a second length, the second length being 10% greater than the first length; and
   a plurality of electrical conductors disposed within the lead body and extending between the proximal end and the distal end, the plurality of electrical conductors are each electrically insulated from each other and form a co-axial coil between the proximal end and the distal end, the co-axial coil comprising:
   an outer coil disposed about an inner coil, the inner coil comprising a first plurality of electrical conductors that are electrically insulated and separated from each other and having a first coil diameter, the outer coil comprising a second plurality of electrical conductors that are electrically insulated and separated from each other and having a second coil diameter, the second coil diameter being greater than the first coil diameter, and the first plurality of conductors being less than the second plurality of conductors, wherein the inner coil has a shear stress value that is substantially equal to the outer coil shear stress.

2. An extensible implantable electrical lead according to claim 1, wherein the first plurality of electrical conductors and second plurality of electrical conductors have substantially the same outer diameter.

3. An extensible implantable electrical lead according to claim 1, wherein the second length is at least 20% greater than the first length.

4. An extensible implantable electrical lead according to claim 1, wherein the second length is at least 25% greater than the first length.

5. An extensible implantable electrical lead according to claim 1, wherein the first plurality of electrical conductors coil in a clockwise direction and the second plurality of electrical conductors coil in a counter-clockwise direction.

6. An extensible implantable electrical lead according to claim 1, wherein the lead body further comprises a sheath disposed between the outer coil and in the inner coil.

7. An extensible implantable electrical lead according to claim 1, wherein the polymeric material comprises silicone.

8. An extensible implantable electrical lead according to claim 1, wherein the first plurality of electrical conductors is 3 conductors and the second plurality of electrical conductors is 5 conductors.

9. An extensible implantable electrical lead according to claim 1, wherein the lead body further comprises a plurality of contacts at the distal end of the lead body and each one of the plurality of electrical conductors connects a single distal end contact or electrode with a proximal end contact.

10. An extensible implantable electrical lead according to claim 1, further comprising a third coil in co-axial relation to the outer coil and inner coil, the third coil having a diameter being different than the first coil diameter and the second coil diameter and including a different number of insulated conductors than the first coil or second coil.

11. An implantable neurostimulation system comprising
   a neurostimulating device; and
   an extensible electrical lead electrically coupled to the neurostimulating device, the extensible electrical lead comprising:
   a lead body having a proximal end and a distal end, the lead body formed of a polymeric material that is extensible between a first length and a second length, the second length being 10% greater than the first length; and
   a plurality of electrical conductors disposed within the lead body and extending between the proximal end and the distal end, the plurality of electrical conductors are each electrically insulated from each other and form a coaxial coil between the proximal end and the distal end, the co-axial coil comprising:

an outer coil disposed about an inner coil, the inner coil comprising a first plurality of electrical conductors that are electrically insulated and separated from each other and having a first coil diameter, the outer coil comprising a second plurality of electrical conductors that are electrically insulated and separated from each other and having a second coil diameter, the second coil diameter being greater than the first coil diameter, and the first plurality of conductors being less than the second plurality of conductors, wherein the inner coil has a shear stress value that is substantially equal to the outer coil shear stress.

12. An implantable neurostimulation system according to claim 11, wherein the extensible electrical lead is a lead extension that electrically couples the neurostimulating device to a proximal end of a lead having a plurality of contacts at a distal end of the lead.

13. An implantable neurostimulation system according to claim 11, wherein the second length is at least 25% greater than the first length.

14. An implantable neurostimulation system according to claim 11, wherein the first plurality of electrical conductors is 3 conductors and the second plurality of electrical conductors is 5 conductors.

15. A method comprising:

applying a force of 5 N or less to a proximal end and a distal end of an extensible electrical lead having a first length, the force increasing the first length of the extensible electrical lead by at least 10%, wherein the extensible electrical lead comprises:

a lead body having a proximal end and a distal end, the lead body formed of a polymeric material that is extensible between a first length and a second length, the second length being 10% greater than the first length; and a plurality of electrical conductors disposed within the lead body and extending between the proximal end and the distal end, the plurality of electrical conductors are each electrically insulated from each other and form a co-axial coil between the proximal end and the distal end, the co-axial coil comprising:

an outer coil disposed about an inner coil, the inner coil comprising a first plurality of electrical conductors that are electrically insulated and separated from each other and having a first coil diameter, the outer coil comprising a second plurality of electrical conductors that are electrically insulated and separated from each other and having a second coil diameter, the second coil diameter being greater than the first coil diameter, and the first plurality of conductors being less than the second plurality of conductors, wherein the inner coil has a shear stress value that is substantially equal to the outer coil shear stress; and removing the force from the extensible electrical lead to return the extensible electrical lead to its first length.

16. A method according to claim 15, wherein the applying step increases the first length by at least 20%.

17. A method according to claim 15, wherein the applying step increases the first length by at least 25%.

18. A method according to claim 15, further comprising implanting the extensible electrical lead in a patient.

\* \* \* \* \*